United States Patent [19]

Beach et al.

[11] Patent Number: 5,738,097
[45] Date of Patent: Apr. 14, 1998

[54] VECTOR DOPPLER SYSTEM FOR STROKE SCREENING

[75] Inventors: Kirk Beach, Seattle; Gerald J. McMorrow, Kirkland; William L. Barnard, Seattle, all of Wash.

[73] Assignee: Diagnostics Ultrasound Corporation, Redmond, Wash.

[21] Appl. No.: 745,271

[22] Filed: Nov. 8, 1996

[51] Int. Cl.$^6$ ........................................ A61B 8/00
[52] U.S. Cl. ........................................ 128/661.09
[58] Field of Search .................. 128/661.01, 661.04, 128/661.08, 661.09, 661.1, 916

[56] References Cited

U.S. PATENT DOCUMENTS 4,062,237  12/1977  Fox ................................. 128/661.01

*Primary Examiner*—George Manuel
*Attorney, Agent, or Firm*—Jensen & Puntigam, P.S.

[57] ABSTRACT

A pulse Doppler system for determining blood flow velocity in a blood vessel in a body, in particular the carotid artery. A sample region covering a section of the artery is investigated, using two spaced transmitters, one with a frequency of 3 MHz and the other with a frequency of 4.5 MHz. The received echo beams are then processed to determine the component blood velocities for each frequency. The two component values are then resolved into a true blood flow velocity for the sample region. That information is used to produce a color-coded velocity map of the artery, which may be conveniently displayed to the operator.

22 Claims, 5 Drawing Sheets

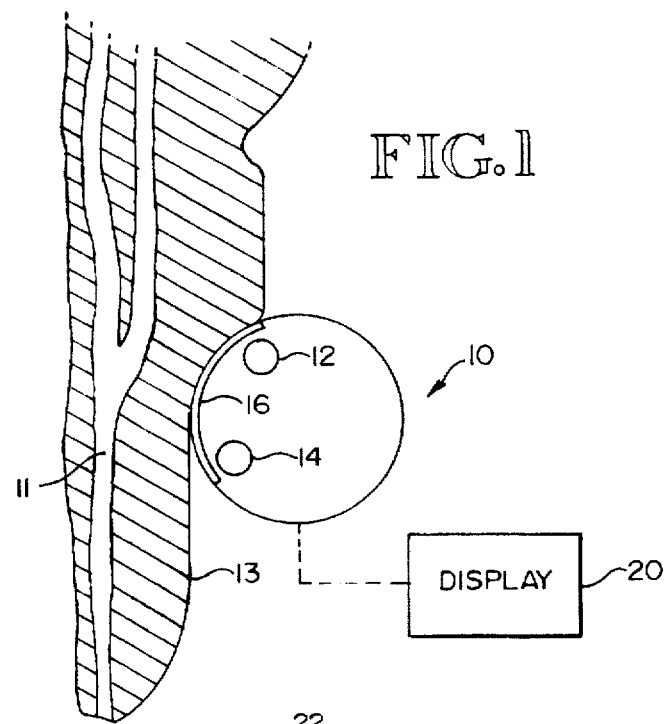
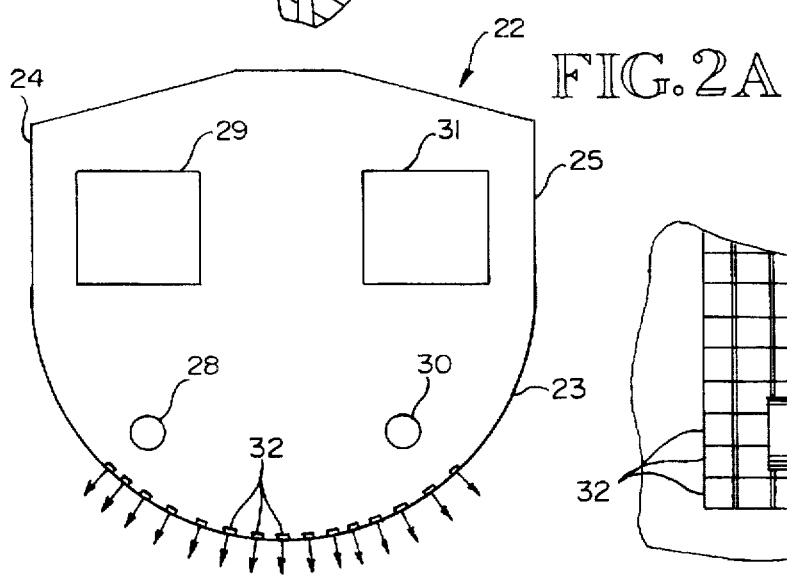
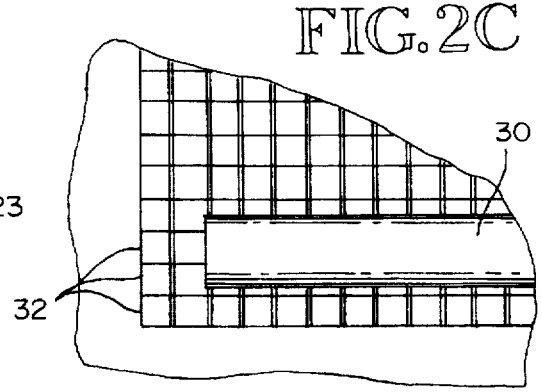
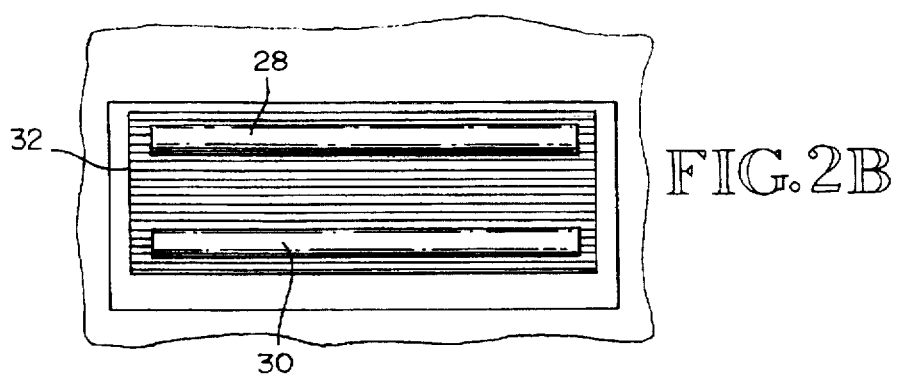

2uS SAMPLING SEQUENCE

F1 ACCUMULATOR 0°:     0,8,16,24,32,40,48,56,64,0,8...
F1 ACCUMULATOR 90°:    2,10,18,26,34,42,50,58,66,2,10...
F1 ACCUMULATOR 180°:   4,12,20,28,36,44,52,60,68,4,12...
F1 ACCUMULATOR 270°:   6,14,22,30,38,46,54,62,70,6,14...
F2 ACCUMULATOR 0°:     0,12,24,36,48,60,0,12...
F2 ACCUMULATOR 90°:    3,15,27,39,51,63,3,15...
F2 ACCUMULATOR 180°:   6,18,30,42,54,66,6,18...
F2 ACCUMULATOR 270°:   9,21,33,45,57,69,9,21...

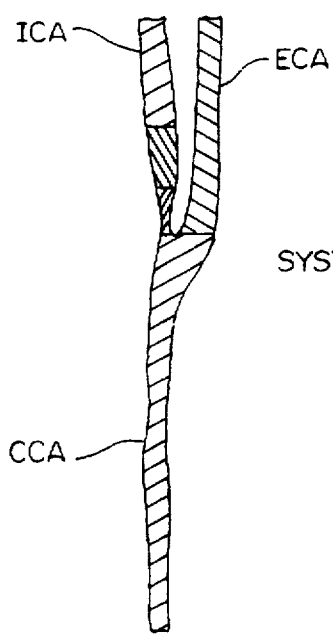
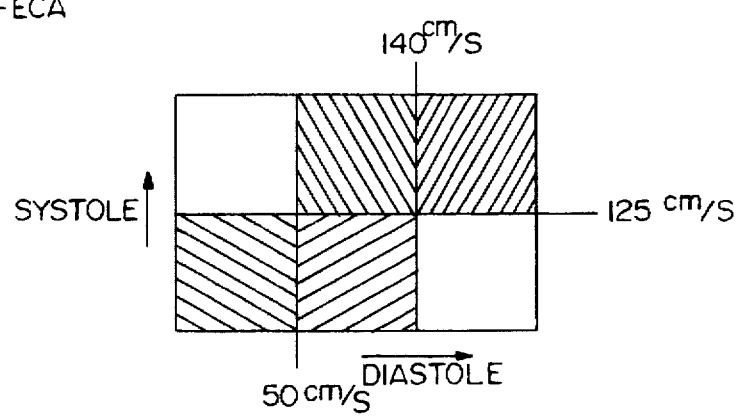
FIG. 10B
FIG. 10A

VECTOR DOPPLER SYSTEM FOR STROKE SCREENING

TECHNICAL FIELD

This invention relates generally to Doppler apparatus for detecting blood vessel velocity, such as in the carotid artery, and more particularly concerns such an apparatus which uses pulsed Doppler signals to measure at least two components of blood velocity in a plurality of voxels (sample volumes) in a sample region, including in an artery, and then to determine therefrom the blood velocity magnitude and heading in each voxel.

BACKGROUND OF THE INVENTION

The medical condition known as "stroke" is generally caused by the presence of a stenosis, i.e. a region of narrowing, in the carotid artery which supplies blood to the brain. Typically, such a stenosis occurs in the vicinity of the bifurcation of the carotid artery in the neck area, at which point an internal branch of the artery extends to the brain and an external branch provides blood to the facial area. It has been estimated that approximately 500 people per day have a stroke in the United States, with approximately 150 people dying immediately and 200 being permanently disabled to varying degrees.

There is a known correlation between the blood velocity through the carotid artery and the extent or seriousness of any stenosis therein. For instance, it is known that for both asymptomatic and symptomatic patients with an internal carotid artery stenosis of greater than 80% diameter reduction (vessel narrowed in diameter by 80%) have a 20% chance of having a stroke within two years, while symptomatic patients having an internal carotid artery stenosis of greater than 50% reduction have a 15% chance of having a stroke within two years. Both of the above patient categories benefit significantly by having surgical treatment for the stenosis, referred to as an endarterectomy.

The traditional method of examining the internal carotid artery for stenosis is selective contrast X-ray angiography. In this examination method, a catheter is used to deliver an X-ray absorbing contrast liquid to the common carotid artery in the neck via the femoral artery in the leg and the aorta. This method, however, in addition to being expensive, carries a 2% complication rate of stroke or other ischemic injury.

In another evaluation technique, a skilled practitioner listens (by means of a conventional stethoscope) to the sound of the blood as it flows through the carotid artery through the stenosis region (referred to as "Bruit" sounds); this technique, however, is quite limited, since some of the Bruit sounds (or lack thereof) are difficult to accurately correlate with specific magnitudes of stenosis. In addition, there are also some ambiguities between the velocity of the blood in the external carotid branch going to the facial area as opposed to the internal carotid branch which goes to the brain. There are ways to distinguish between the two, but it does add an additional complicating factor to the stethoscope means of determination.

Sometimes evaluation of stenosis in the carotid artery is done with two-dimensional real time ultrasound B-mode imaging, although this method is not routinely used for screening patients, because the examination is expensive, requiring sophisticated apparatus, an expert examiner and a relatively long time (15–20 minutes) for a typical (normal) examination and up to 60 minutes for a non-routine (abnormal) examination. In addition, high sensitivity ultrasound cannot differentiate relevant carotid stenotic disease (50%–79 diameter reduction and 80%–99% diameter reduction) from mild disease.

Various Doppler systems have also been used to determine blood velocity, including the blood velocity in the carotid artery. In the Doppler techniques, a shift in frequency of a returning signal is used to determine both velocity and direction of blood flow. However, blood flow through an artery, including the carotid artery, is quite complex, and more resembles a helical pattern as opposed to a straight axial flow. Hence, the direction of blood flow will vary widely, depending upon the particular region of the artery being investigated.

This complex pattern of blood flow in an artery will significantly affect the accuracy of blood velocity determinations by Doppler techniques. Conventionally, a Doppler transmitter/receiver device is moved about until it is oriented where a maximum Doppler frequency shift value is obtained; in this position, the sample volume is within the residual or open portion of the carotid artery, i.e. that portion of the artery not blocked by stenosis.

The task of orienting the Doppler device to the most appropriate angle relative to the artery is always problematic, and even at the best angle, the resulting magnitude of blood velocity is not completely accurate relative to a true blood velocity determination. Typically, imaging techniques are used to obtain the desired angle, 60° is a standard or typical angle used. Achieving a proper angular position for the transmitter/receiver is critical to obtaining reliable results with such a system. This "Doppler angle" problem between the direction of the Doppler ultrasound beam and the direction of blood flow in the artery remains yet to be solved in order to provide an accurate, dependable determination of true blood velocity in an artery.

A number of patents/articles have attempted to address various issues of blood flow using Doppler techniques. These include U.S. Pat. No. 4,062,237 to Fox, which teaches a cross-beam ultrasonic flow meter using two pairs of ultrasonic beam-transmitting elements. This device, however, is continuous wave Doppler and is not capable of addressing complex blood flow patterns, because of a lack of depth discrimination. A similar example, among several others, is shown in an article entitled "A Double Beam Doppler Ultrasound Method for Quantitative Blood Flow Velocity Measurement", by Wei-qi et al.

Other relevant patents include U.S. Pat. No. 4,688,430 to Anderson, which teaches a three-dimensional imaging apparatus, as well as U.S. Pat. No. 4,217,909 to Papadofrangakis et al, which teaches the use of quadrature components and real-time processing to determine direction of blood flow in an artery. U.S. Pat. No. 5,398,216 to Hall et al teaches a two-dimensional blood flow apparatus used for blood flow imaging. Most recent is U.S. Pat. No. 5,409,010 to Beach et al, directed toward determining the angular heading and magnitude of velocity of complex blood flow.

As indicated above, however, none of the above reference devices has been successful in providing accurate three-dimensional information concerning blood flow across an artery such as the carotid artery. In addition, the ultrasonic screening procedures currently used for carotid artery evaluations are slow and expensive. Accordingly, there remains a significant need for a fast, accurate and low cost means for a carotid artery stenosis screening, capable of detecting very quickly (within a few seconds) peak systolic velocity and end diastolic velocity. The process furthermore should be sufficiently fast to capture the entire cardiac cycle.

DISCLOSURE OF THE INVENTION

Accordingly, the invention is an apparatus for determining velocity of blood in a sample region traversed by a blood vessel in which the blood is flowing, comprising: means for transmitting a first ultrasound signal burst having a first carrier frequency into a plurality of voxel portions of the sample region; means for transmitting a second ultrasound signal burst having a second carrier frequency which is orthogonal relative to the first carrier frequency into said voxel portions of the sample region; means for receiving echo signals from blood flowing in said voxel portions for both first and second transmitted ultrasound bursts; means for processing the echo signals from said first and second ultrasound bursts to obtain blood velocity component values from each of said voxel portions in said sample region; and means for combining the velocity component values for each of said voxel portions to produce blood velocity information for each of said voxel portions.

BRIEF DESCRIPTION OF THE DRAWINGS

FIG. 1 is a diagram showing the apparatus described herein in longitudinal section relative to the carotid artery.

FIG. 2A is a more detailed cross section of a portion of the apparatus described herein.

FIG. 2B is a side elevational view of the apparatus of FIG. 1.

FIG. 2C is a side elevational view of a portion of an alternative embodiment to that of FIG. 1.

FIGS. 10A and 10B show an example of a display produced by the apparatus discussed below indicating blood flow through a stenosis in a carotid artery.

BEST MODE FOR CARRYING OUT THE INVENTION

Figures 3, 5:
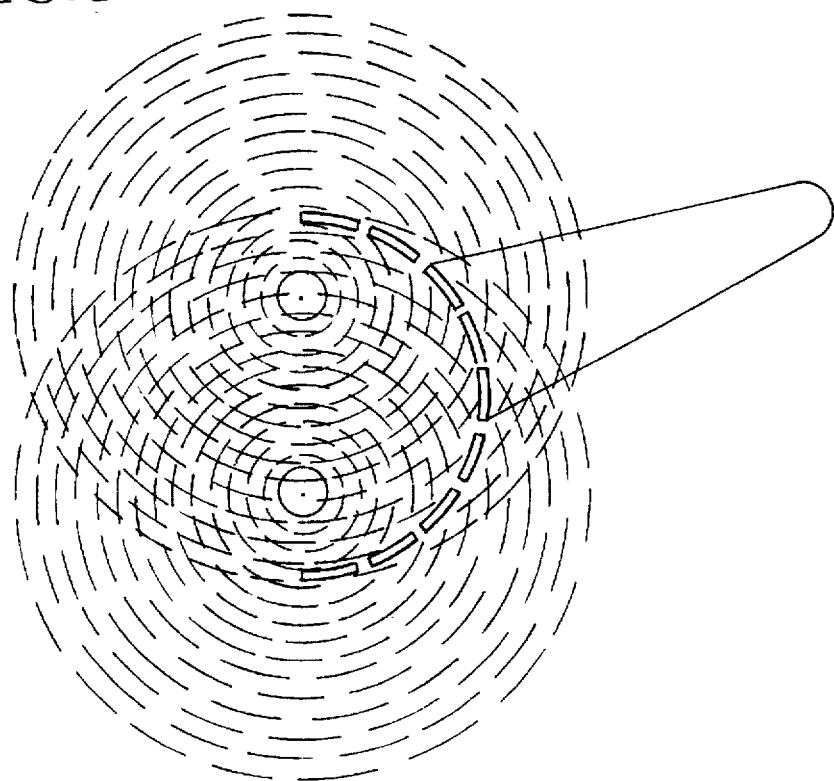
FIG. 3 is a simplified view of the Doppler signal transmission and return patterns of the apparatus of FIG. 2.
FIG. 5 is a chart showing the sampling sequence for the apparatus disclosed herein.
Figure 4:
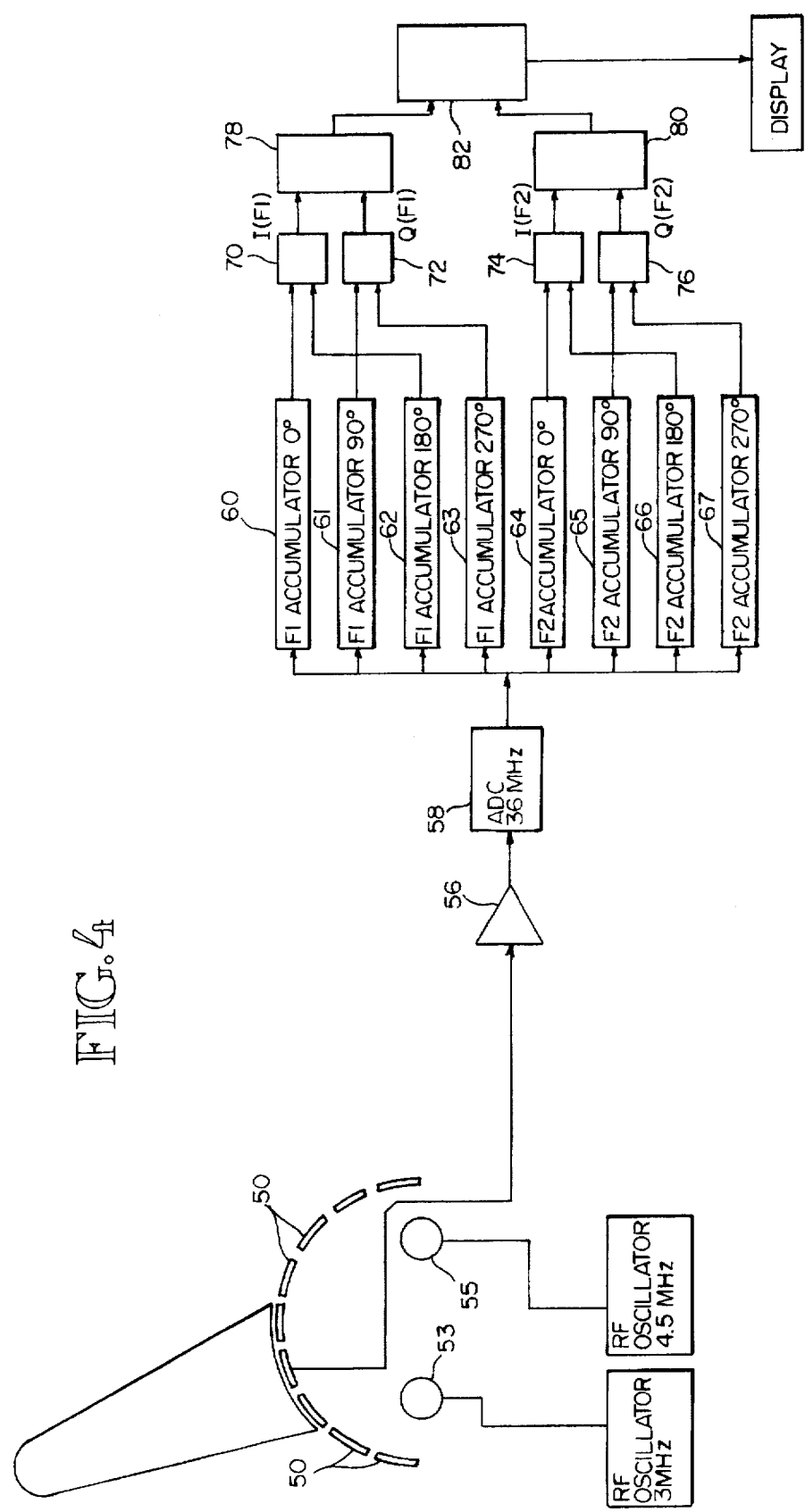
FIG. 4 is a block diagram showing the circuit of the apparatus disclosed herein.

The apparatus described herein (FIG. 1) includes a handheld transducer head which is positioned by an operator (only minimal training required) generally in a horizontal position under the left or right side of the jaw with the cylinder axis perpendicular to the carotid artery under examination 11, adjacent the neck 13 of a patient. In the embodiment shown, the transducer head, shown generally at 10, includes Doppler transmitting elements 12, 14, Doppler receiving elements 16, and the signal processing software. The results produced by the signal processing are applied to a two-dimensional display apparatus 20, such as a computer monitor, which will show the results of the Doppler scan by means of different colored regions within the artery, each color indicating a different blood velocity value.

In the particular embodiment of FIG. 2, the transducer head shown generally at 10 has a diameter of approximately 80 millimeters and a length of approximately 50 millimeters, such that an operator can easily position the scanner under a patient's jaw, against the neck. With the system of the present invention, the probe must be generally positioned within a range of ±30° perpendicular to the carotid artery. This is a large range, easily obtained by even an inexperienced operator; the embodiment described herein is thus not susceptible to the angular position criticality of other Doppler ultrasound blood flow devices, as described above.

In the specific embodiment of FIG. 2, the transducer body 22 includes a hemicylindrical half section 23, forming a front portion of the probe and two parallel sides 24, 25 extending rearwardly of the hemicylindrical section. Rear side 26 includes a small flat central portion and two straight side portions which incline slightly from the edges of the parallel sides 24, 25 to the opposed edges of the central portion of rear side 26.

Contained within body 22 are two spaced transmitters 28 and 30, a plurality of receivers 32—32 which extend longitudinally of the probe in the form of thin (4 mm) parallel strips on the face of hemicylindrical section 23. The transmitter electronics and the receiver electronics are also contained within the probe body and are shown generally at 29 and 31. Typically, the transmitter and receiver electronics will be in the form of a plurality of conventional PCB boards mounted within the body 22.

The two transmitters 28 and 30 are substantially identical, except that in the embodiment shown, the operating frequency of one transmitter is 3.0 MHz, while the other is 4.5 MHz. The two frequencies are "orthogonal", which is a well-known term in this particular art, generally to the effect that the sample period for an orthogonal frequency is equal to 1/difference between the two frequencies. Each transmitter will be a PZT5A element shaped into a 6.3 diameter tube. The outer surface of each transmitting tube will be segmented longitudinally into 25 successive transducer portions, with each segment being approximately 2 mm wide. In the embodiment shown, the transmission could be either omni-directional, i.e. around the entire circumference of the tube, or it could be restricted to a particular "active" angle, for instance, 100°.

In operation of the embodiment shown, three adjacent segments of the transmitting rods are energized in parallel, successively along the length of the rod. Each segment group is energized for a duration of two microseconds, during which time a certain number of signal cycles is produced, depending upon whether the ultrasound transmitting frequency is 3 MHz or 4.5 MHz. The pulse repetition rate or frequency is approximately 12.5 KHz.

This arrangement results in the insonification of a plane of a spatial volume (sample region) which includes the full longitudinal section of the carotid artery, when the device is operatively positioned. In the embodiment shown, the sample region is approximately 30 mm deep (between 10 mm and 40 mm), approximately 130 mm long and approximately 50 mm wide. In this particular spatial volume, the individual Doppler voxel (or sample volume) will be approximately 2 mm by 2 mm by 1 mm in depth. As used in this application, the term "voxel" refers to the volume in tissue that is defined along the depth dimension of the ultrasound beam by the duration of the transmitted ultrasound pulse and the time duration of the receive gate and in the lateral dimension (perpendicular to the depth dimension) by the focal characteristics of the transmit transducer beam pattern superimposed on the receive transducer pattern.

Thus, in operation, the transmitter produces a signal "burst" of ultrasound directed within a fan-shaped plane of the sample region which may include the carotid artery in the plane. Echoes from 80 voxels along each of 20 lines radiating from each of 20 receiving transducers provide I/Q quadrature phase data from each of the 1600 voxels in the plane for each of the two transmitting tubes. A group of three or more transmit bursts, each separated by 80 microseconds (spanning a period of 240 microseconds) permits the acquisition of a triad of I/Q quadrature phase data for each of the 1600 voxels required to perform a vector velocity determination for each voxel in the plane. Successive transmit element groups (of three elements) are energized along the rod (25 elements, each element 2 mm wide) to span a width of 46 millimeters with 23 planes. At least four of those planes will include the carotid artery which is 8 mm in diameter. The entire acquisition of vector velocity data from the 368,000 voxels (23*16,000) requires a minimum of 5.76 milliseconds, allowing 200 acquisitions of vector velocity data from all voxels every 1.152 seconds over a volume which spans 30 mm deep, 130 mm high and 50 mm wide, and with an individual voxel volume of 2 mm by 2 mm by 1 mm deep, such that four voxels span the diameter (width) of the carotid artery and eight span the depth of the artery. The total number of voxels for the above sample volume will be approximately 40,000.

The ultrasound signals for each of the two transmitting transducers, one at a frequency of 3 MHz and the other at a frequency of 4.5 MHz, are transmitted simultaneously to the sample volume. The ultrasound signals are reflected back to the transducer head by the flowing blood and are received by the plurality of receiver transducers 32 (FIG. 2B). In the embodiment shown, there are a total of 20 receiving transducers, in the form of parallel receiver strips 32 which extend longitudinally of the transducer head and are hence aligned generally orthogonal relative to the carotid vessel when the scanner probe is in proper position. Each of the receiver strips will be approximately 4 mm wide, positioned on the 4 cm (radius) curved surface portion 23 of the transducer head. The characteristics of the receiving transducer's beam pattern as it spreads in the Fraunhoffer zone of the beam pattern generally matches the spreading which would occur by virtue of the curved surface. FIG. 3 shows a simplified diagram showing the combined signal transmission pattern of both transmitters and a received beam pattern.

It should be understood, however, that there can be various receiver configurations. For instance, the receiver could be arranged to slide mechanically along the transducer head. The receiver could be, in effect, two-dimensional. In addition, each receiver strip could be segmented (FIG. 2c) such as into 25 segments, adjacent receiver elements. Each element would be separated by a few thousandths of an inch. The receiver thus forms a matrix of elements, with all of the elements receiving the returning signal simultaneously. In such an embodiment, the transmitters 28, 30 could be single, solid tubes.

After the reflected beam data is received, i.e. acquired by the individual receiving transducers, it is initially processed to provide I and Q values for both of the transmitted frequencies. The I and Q values are the orthogonal cross-products, i.e. sum and difference signals, resulting from the demodulation of the received signals. In demodulating the received signals, the in-phase demodulation result for the transmit (reference) signal against the received signal is the "I" signal, while the result of the quadrative demodulation, i.e. where the reference signal is 90° removed, is the "Q" signal.

There are many ways of obtaining the I and Q signals. In one embodiment, the received signal is applied to a series of time gates, so that it can be identified with respect to the proper depth within the artery of the particular voxel from which the echo signal is returning. These received signals are then applied both against an in-phase transmit or reference signal to produce the in-phase demodulation and a delayed reference signal, to produce the quadrature demodulation.

The transmit beams, at 3 MHz and 4.5 MHz, from transmit tubes 53, 55, respectively, are reflected back to receiving transducers 50—50. The signals are then amplified by amplifier 56 and then applied to an analog-to-digital converter 58. In the embodiment shown, the analog-to-digital converter 58 is clocked at a 36 MHz rate such that each transmitted and received Doppler signal is sampled at least four times per cycle. The 3 MHz transmitter frequency requires a 12 MHz sampling signal, while the 4.5 MHz transmitter frequency requires an 18 MHz sampling signal.

The signals are then applied to a plurality of accumulators 60-67. There are four accumulators for each transmit frequency, where frequency F1 is 3 MHz and frequency F2 is 4.5 MHz. The four accumulators are clocked so that they sample the transmit signal at zero, 90°, 180° and 270° phases. The sampling sequence for the accumulators is shown in FIG. 5. The in-phase I signal for the 3 MHz transmitting frequency will be the difference between the zero and 180° phases produced by difference circuit 70, while the quadrature Q data is the difference between the 90° and 270° phases, produced by difference circuit 72. The I and Q values for the 4.5 MHz signal are similarly produced by difference circuits 74 and 76, respectively.

While accumulators are used to achieve the I and Q values in the embodiment shown, it should be recognized that there are various other electronic signal processing techniques to obtain the I and Q data.

The I and the Q data at the output of the difference circuits for both frequencies will then be processed by auto-correlation processors 78 and 80 to yield the vector components of blood velocity (if blood flow is present or a zero reading if blood flow is absent) for each voxel along each receiving beam pattern within the plane insonified by the transmitted Doppler signals. Auto-correlation techniques are well known, so no detailed explanation is provided. A fast fourier transformer (FFT) or short fourier transformer may also be used. In the present invention, the two separate ultrasound frequencies transmitted from different locations into each voxel provides component values which are processed according to FIG. 9, which eliminates the angle dependency of previous blood flow determining systems by combining the characteristic component magnitudes of each transmitted beam to produce a true blood velocity vector value. This is carried out in calculation circuit 82 and can be understood as follows.

When a conventional Doppler system measures the particular component of blood velocity in the direction parallel to the axis of the ultrasound transmit-echo signal path, the magnitude of this particular velocity component is understood to be less than the magnitude of the true velocity vector. The combination of two blood velocity components can yield the true blood velocity vector (referred to generally herein as "true blood velocity") within a plane in that particular voxel. Further, the combination of three blood velocity components which are not coplanar can yield the true velocity vector in three dimensions in that particular voxel.

Figure 6:
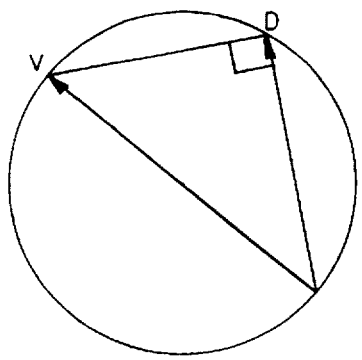
FIGS. 6–9 are vector diagrams illustrating the velocity theory of the apparatus disclosed herein.
Figure 7:
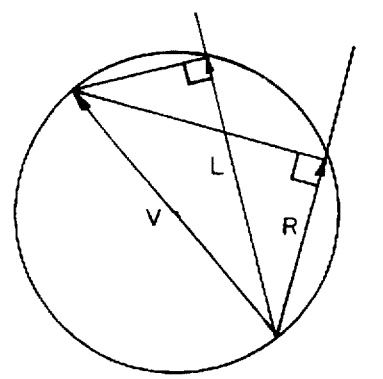

For a "true" blood velocity having a particular magnitude and heading, the various velocity components comprising that true blood velocity vector can be thought of as being located on a sphere, with the true velocity vector being the diameter of the sphere. FIG. 6 shows a two-dimensional view of such a sphere, showing a true velocity vector 86 and one measured component thereof 88. If two velocity components of blood flow are known, the diagram of FIG. 6 changes to the diagram of FIG. 7. The important point is that the two components 90, 92 of the true blood velocity vector 94 are related geometrically; hence, if the magnitudes L and R, respectively, of components 90 and 92 are known, the component of the velocity vector component 94 in the plane shared by components 90 and 92 can be computed by using known geometric and trigonometric relationships, using the L and R magnitudes of the two component values.

Thus, as long as the cylindrical axis of the transducer head is oriented perpendicularly to the direction of the carotid artery (which can be achieved by placing the transducer head against the jaw), the true velocity magnitude along the carotid artery can be obtained as a function of distance along the external and internal carotid artery branches.

Figure 8:
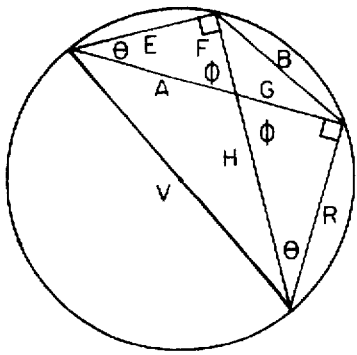

The "proof" or derivation of the above principle is set forth below. Referring to FIG. 8, the triangle comprising sides AFE is similar to the triangle comprising sides HGR, where A/F=H/G and A/H=F/G. Further, the triangle comprising sides AHV is similar to triangle FGB, where V/H=B/G. In regard to FIG. 8, both of those triangles are right angle triangles and hence angles $\Theta$ in each of those triangles are equal as well as the remaining angle. In triangles AHV and FGB, the angles n in each triangle are also equal, while the triangles themselves are proportional. Using known trigonometric relationships, including the law of cosines (equation 2), where V=true velocity and L (sum of H+F in FIG. 8) and R are magnitude values of the two velocity components:

$$V*G/H = B = V*\operatorname{Sin}\Theta \tag{1}$$

$$B^2 = L^2 - 2*L*R\cdot\operatorname{Cos}\Theta + R^2 \tag{2}$$

where the * operator reflects both real and imaginary values. Thus, $$V^2*\operatorname{Sin}^2\Theta = L^2 - 2*L*R\cdot\operatorname{Cos}\Theta + R^2 \tag{3}$$

Since angle $\Theta$ (the angle between the two transmit-echo ultrasound propagation vectors is a fixed value and known, for a particular arrangement of transducers, as is true for the embodiment herein, the values of $\operatorname{sine}^2\Theta$ and $\operatorname{cosine}\Theta$ are also fixed values (and known), so that the magnitude of the true velocity vector V depends basically only on the magnitudes of the two components of the transmit-echo ultrasound signals, i.e. the 3 MHz and 4.5 MHz signals of the embodiment shown. Hence, the magnitude of the true velocity vector can be computed without knowing its particular heading, including its angle.

Referring still to FIG. 8, if the two velocity components are acquired by separate receivers and the center of the circle is designated by coordinate values a,b, the radius of the circle is V/2 and the X and Y axis values of the termination point (magnitude) of V will be 2a, 2b. For any point X,Y on the circle, then:

$$(X_i-a)^2 + (Y_i-b)^2 = (V/2)^2 \tag{4}$$

since $$a^2 + b^2 = (V/2)^2$$

then $$X_i^2 - 2*X_i*a + Y_i^2 - 2*Y_i*b = 0 \tag{5}$$

Figure 9:
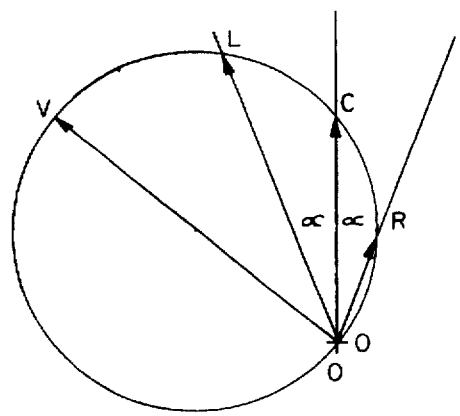

Referring to FIG. 9, a line C bisects angle $\Theta$ between the two transmitters. Setting angle $\alpha=\Theta/2$, as shown in FIG. 9, the X and Y coordinates for magnitude L of one component (component 90 in FIG. 7) are:

$$X_l = L*\operatorname{Sin}\alpha \tag{6}$$

$$Y_l = L*\operatorname{Cos}\alpha \tag{7}$$

and the X and Y coordinates of magnitude R of the second component are:

$$X_r = -R*\operatorname{Sin}\alpha \tag{8}$$

$$Y_r = R*\operatorname{Cos}\alpha \tag{9}$$

Then, to solve for velocity values Vx and Vy using trigonometric relationships:

$$L^2*\operatorname{Sin}^2\alpha - 2*a*L*\operatorname{Sin}\alpha + L^2*\operatorname{Cos}^2\alpha - 2*b*L*\operatorname{Cos}\alpha = 0 \tag{10}$$

and $$L^2*(\operatorname{Sin}^2\alpha + \operatorname{Cos}^2\alpha) - 2*a*L*\operatorname{Sin}\alpha - 2*b*L*\operatorname{Cos}\alpha = 0 \tag{11}$$

Similarly $$L - 2*a*\operatorname{Sin}\alpha - 2*b*\operatorname{Cos}\alpha = 0 \tag{12}$$

and $$R + 2*a*\operatorname{Sin}\alpha - 2*b*\operatorname{Cos}\alpha = 0 \tag{13}$$

By adding or subtracting the two equations:

$$V_x = 2*a = (L-R)/2*\operatorname{Sin}\alpha \tag{14}$$

$$V_y = 2*b = (L+R)/2*\operatorname{Cos}\alpha \tag{15}$$

The (L−R) and (L+R) values are the quadrature signals which may be obtained in various ways, including electronically. As equations 14 and 15 show, these quadrature values may be used to determine the coordinate value of V (true velocity). Hence, what is referred to herein as true blood velocity may be determined from known components thereof. The resulting value of velocity (V) for one voxel in the sample volume is then combined with surrounding voxel values to provide an overall "map" of blood flow velocity in the sample volume. This velocity map may then be displayed as shown in FIG. 10 for the artery being examined. The various regions of velocity are differentiated by different colored regions on the display.

In the embodiment shown, voxels with peak (systolic) velocities less than 125 cm/sec in the cephalad direction will be colored green, indicating no stenosis greater than 50% diameter reduction according to published correlations between angiography and Doppler studies. Voxels with continuous maximum velocities greater than 140 cm/sec in the cephalad direction will be colored red, indicating a carotid stenosis of greater than 80% diameter reduction but less than 99% diameter reduction according to published correlations between angiography and Doppler studies. Voxels with mean velocities away from the cephalad direction will be colored blue, indicating venous flow returning to the heart or retrograde flow which sometimes occurs in the external carotid artery, and the remaining voxels showing blood flow will be colored yellow, indicating an intermediate stenosis of 50% to 79% diameter reduction according to published correlations between angiography and Doppler studies. Voxels with no blood flow will not be colored and will appear transparent in projection. Other color arrangements can be utilized as well.

A map of the course of the common carotid artery bifurcating into the internal carotid artery and the external carotid artery will be displayed on a screen and a printed record. Using the automatically detected axes of the three arteries at the bifurcation, the projection of the image will be on the plane shared by the arteries, avoiding overlying the external carotid on the internal carotid artery. Annotation lines will show the location and orientation of the skin of the neck and the line of the jaw. FIG. 10 shows an example of a typical blood flow pattern in an artery with a stenosis region in the internal carotid arterial branch. With such a display and a knowledge of the correlation between the colors in the display and the blood velocity, the operator, even one with little training, can quickly ascertain whether a carotid stenosis is present in the carotid artery by simply determining whether a portion of the carotid artery pathway to the brain is either colored red (indicating that carotid endarterectomy surgery would be of benefit in any patient according to the latest clinical trial information) or yellow (indicating that carotid endarterectomy surgery would be of benefit if the patient is having symptoms on the side of the brain ipsilateral to the stenosis).

One of the advantages of the apparatus of the present invention is its speed of operation, which samples at a sufficient rate to capture a complete cardiac cycle from all 368,000 voxels with a time resolution in each voxel of nearly 50 samples per second.

Hence, an apparatus has been described which utilizes conventional pulse Doppler techniques to produce velocity component magnitudes from two different transmitters using different frequencies. The two component values for each voxel are then used to produce a true velocity value for that voxel. The voxel velocity values are then used to produce a velocity map of the sample volumes surrounding the artery. This approach eliminates the angle dependency problem between the ultrasound device and the artery, since the calculation of velocity becomes dependent upon the angle of separation between the two transmitters, which remains fixed. Hence, a fast, relatively inexpensive technique for evaluating carotid artery stenosis is made possible by the present invention, as defined in the claims.

Although a preferred embodiment of the invention has been disclosed herein for illustration, it should be understood that various changes, modifications and substitutions may be incorporated in such embodiment without departing from the spirit of the invention, which is defined by the claims which follow.

What is claimed is:

1. An apparatus for determining velocity of blood through that portion of a sample region traversed by a blood vessel in which the blood is flowing, comprising:
   means for transmitting a first ultrasound signal burst having a first carrier frequency into a plurality of voxel portions of the sample region;
   means for transmitting a second ultrasound signal burst having a second carrier frequency which is orthogonal relative to the first carrier frequency into said voxel portions of the sample region;
   means for receiving echo signals from blood flowing in said voxel portions for both first and second ultrasound signal bursts;
   means for processing the echo signals from said first and second ultrasound bursts to obtain blood velocity component values from each of said voxel portions in said sample region; and
   means for combining the velocity component values for each of said voxel portions to produce true blood velocity information for each of said voxel portions.

2. An apparatus of claim 1, wherein said true blood velocity information is blood velocity magnitude and heading.

3. An apparatus of claim 1, including means for controlling the first and second transmitting means and the receiving means so as to obtain velocity component values from a sufficient number of voxel portions to substantially cover the sample region, wherein the sample region extends the entire depth of the blood vessel.

4. An apparatus of claim 3, wherein the sample region is approximately 30 mm deep, 130 mm long and approximately 50 mm wide.

5. An apparatus of claim 1, wherein the first frequency is approximately 3 MHz and the second frequency is approximately 4.5 MHz.

6. An apparatus of claim 1, including means responsive to said echo signals for determining the relative depth of successive portions of the sample region across the depth of the vessel.

7. An apparatus of claim 1, including means for assigning different colors for selected ranges of true blood velocity values and for producing a velocity map, by color, of the sample region.

8. An apparatus of claim 1, wherein the processing means includes means for determining true blood velocity information at several points in the cardiac cycle.

9. An apparatus of claim 1, including a transducer head member containing said first and second transmitting means and said receiving means, the transducer head member being easily positionable by an operator adjacent to and generally orthogonal to said blood vessel.

10. An apparatus of claim 1, wherein the blood vessel is the carotid artery.

11. An apparatus of claim 1, wherein the first and second transmitting means comprise separate tube-like elements, each tube-like element comprising a plurality of individual transducer elements, wherein the first and second transmitting means are separated by a known distance so that the resulting angle between the first and second ultrasound signal bursts is fixed and known.

12. An apparatus of claim 11, wherein there are approximately at least 25 separate transducer elements in each transmitting means.

13. An apparatus of claim 11, including means for energizing successive groups of transducer elements along the transmitting tube.

14. An apparatus of claim 1, wherein the receiving means includes a plurality of receiving elements in the form of elongated strips which extend longitudinally along a selected part of the transducer body member.

15. An apparatus of claim 14, wherein all of the elongated strips receive echo signals simultaneously.

16. An apparatus of claim 14, wherein the elongated strips are segmented, such that the receiving means defines a matrix.

17. An apparatus of claim 16, wherein the first and second transmitting means are each undivided elements.

18. An apparatus of claim 14, wherein said selected part of the transducer head member has a curvature orthogonal to the receiving elements approximately equal to the spreading of the echo beam pattern.

19. An apparatus of claim 14, including approximately at least 20 receiving elements.

20. An apparatus of claim 1, wherein the receiving means is in the form of a plurality of separate receiving elements, adapted to receive said echo signals simultaneously, thereby defining a receiving matrix.

21. An apparatus of claim 20, wherein the first and second transmitting means are each single, unitary elements.

22. An apparatus of claim 1, wherein said processing means includes means for amplifying the echo signals, means for analog-to-digital conversion of the echo signals and means for applying the echo signals for each frequency to four accumulators, each accumulator shifting the phase of the echo signal by an additional 90°, means for combining the outputs of the 0° and 180° accumulators and for combining the outputs of the 90° and 270° accumulators to obtain I and Q values, and means for determining said blood velocity component values from the I and Q values.

* * * * *